United States Patent [19]

Berkowitz et al.

[11] 4,031,091

[45] June 21, 1977

[54] PROCESS FOR PURIFYING CRUDE CYANURIC ACID

[75] Inventors: Sidney Berkowitz, Highland Park; John D'Angelo, Old Bridge, both of N.J.

[73] Assignee: FMC Corporation, Philadelphia, Pa.

[22] Filed: Dec. 29, 1975

[21] Appl. No.: 644,573

Related U.S. Application Data

[62] Division of Ser. No. 447,824, March 24, 1974.

[52] U.S. Cl. .................................... 260/248 A
[51] Int. Cl.$^2$ .................................... C07D 251/32
[58] Field of Search ........................ 260/248 A

[56] References Cited

UNITED STATES PATENTS

| | | | |
|---|---|---|---|
| 3,357,979 | 12/1967 | Sobocinski et al. | 260/248 |
| 3,380,667 | 4/1968 | Moore et al. | 260/248 X |
| 3,644,359 | 2/1972 | Mesiah et al. | 260/248 |

OTHER PUBLICATIONS

"Handbook of Chemistry & Physics", Ed. 41, Chemical Rubber Pub. Co. Ohio, p. 3363 (1960).

Primary Examiner—John M. Ford
Attorney, Agent, or Firm—Gary M. Nath; Frank Ianno

[57] ABSTRACT

Process for purifying crude cyanuric acid whereby crude cyanuric acid is digested with an aqueous phosphoric acid solution containing about 10 to about 85% phosphoric acid at a temperature of about 180° to about 220° C under at least the autogenously developed pressure to digest the crude cyanuric acid. A novel, large, free-flowing cyanuric acid product is recovered free of any hard cement-like masses.

1 Claim, 2 Drawing Figures

PROCESS FOR PURIFYING CRUDE CYANURIC ACID

This is a division of application Ser. No. 447,824, filed Mar. 4, 1974.

This invention relates to the purification of crude cyanuric acid with aqueous phosphoric acid solutions at high temperatures. This invention also relates to the formation of novel, free-flowing cyanuric acid crystals.

Cyanuric acid has the empirical formula $C_3H_3O_3N_3$ and is the main product produced by heating urea, biuret or mixtures of both in a kiln at temperatures of about 200° to about 350° C. Unfortunately, the product produced is composed of only about 75% cyanuric acid with the remainder of the product containing about 25% ammelide impurities and minor amounts of other impurities such as ammeline. This product mixture is conventionally referred to as crude cyanuric acid. Since it is quite difficult to separate the crude cyanuric acid into its component parts in order to recover pure cyanuric acid, various methods have been proposed to purify the cyanuric acid by converting the impurities into cyanuric acid by acid hydrolysis. This conversion by acid hydrolysis is sometimes referred to as the acid digestion process.

The acid digestion process comprises mixing crude cyanuric acid with a strong mineral acid to give a slurry containing 10 to 15% undissolved solids. The mineral acids disclosed as being operative are sulfuric, hydrochloric, nitric and phosphoric acid, with sulfuric acid being preferred. The slurry is digested at reflux temperatures (about 104° C) for 1 to 10 hours. This digestion in hot mineral acid results in the hydrolysis of most of the impurities to cyanuric acid. Methods employing this procedure are described in U.S. Pat. Nos. 2,943,088 and 3,107,244. Higher temperatures, up to about 130° C, may be employed if superatmospheric pressures up to 100 p.s.i. are employed. See U.S. Pat. No. 3,107,244. The use of temperatures above 165° C has also been suggested with strong mineral acids, such as sulfuric acid, in U.S. Pat. No. 2,768,167.

Because the acid digestion process involves heating and mixing a thick slurry of solids in a digester vessel for long periods of time, some problems are encountered. Mixing in the digester vessel is often difficult and a constant build-up of solids on the walls of the digester results. Frequently, large chunks of this solid build-up break away from the walls and either plug the exit lines or bend the agitator. Furthermore, strong mineral acid reaction mixtures held at operating temperatures for prolonged periods can result in partial hydrolysis of the cyanuric acid to ammonia and carbon dioxide, thus decreasing cyanuric acid yields.

Additional problems result when hydrochloric acid or phosphoric acid have been employed at conventional operating temperatures rendering the use of either of these acids commercially impractical. Commercial operation of a hydrochloric acid digestion process is extremely difficult and hazardous and results in many shut downs because of equipment breakdown and corrosion. Commercial operation of a phosphoric acid digestion process has not been heretofore possible because of the slow impurity conversion rate and because the cyanuric acid is partially hydrolyzed to ammonia and carbon dioxide over the prolonged digestion period. Furthermore, the reaction rate with phosphoric acid is approximately five times slower than with strong mineral acids, such as sulfuric acid. The use of higher temperatures, up to about 130° C, by the prior art, has not alleviated these difficulties.

The sulfuric acid and nitric acid digestion processes, while being commercially effective processes, have caused numerous pollution problems with regard to the separated acid digestion solution. The separated acid digestion solution has been partially or entirely discarded as an untreated waste stream since treatment to render them safe for discharge is difficult and expensive. Untreated acid digestion solutions discharged into natural water ways, however, disrupts and often destroys natural fauna and flora.

In addition to the above acid digestion process deficiencies, the cyanuric acid product produced by these processes is often difficult to separate from the acid digestion solution and difficult to handle once separated because of the samll crystals produced. The crystals generally have particle sizes between about 30 and 50 microns. Crystals of this size must be filtered carefully to prevent valuable cyanuric acid crystals from passing through conventional separating means along with the filtrate.

It has been unexpectedly discovered that crude cyanuric acid can be purified by mixing sufficient amounts of crude cyanuric acid with an aqueous phosphoric acid solution containing about 10 to about 85% phosphoric acid to form a 10 to 45% crude cyanuric acid slurry, heating the slurry to a temperature of about 180° to about 220° C under at least the autogenously developed pressure to digest the crude cyanuric acid, cooling the digested cyanuric acid to precipitate the cyanuric acid crystals, and recovering the precipitated cyanuric acid crystals.

The process of this invention permits the purification of crude cyanuric acid in a commercially simple and efficient manner without the need for large expensive digester reactors. It permits the recovery of cyanuric acid in exceptionally high yields and exceptionally high purities in relatively short periods of time, that is in less than 60 seconds. It unexpectedly results in the formation of a cyanuric acid product which contains at least 90% cyanuric acid crystals having particle sizes between 60 and 650 microns. Furthermore, the invention permits the treatment of the acid digestion solution effluent in a simple and efficient manner to produces useful by-products.

Figure 1:
FIG. 1 is a photomicrograph of cyanuric acid crystals formed from crude cyanuric acid digested with phosphoric acid according to the invention.

In the process of the invention, crude cyanuric acid containing ammelide and other minor impurities is mixed with an aqueous phosphoric acid solution. The aqueous phosphoric acid solution dissolves all acid-soluble impurities present in the reaction mixture. It hydrolyzes ammelide to yield cyanuric acid and a corresponding ammonium salt, that is, ammonium phosphate. Additionally, ammonium cyanurates are hydrolyzed to yield cyanuric acid and the corresponding ammonium salt.

The crude cyanuric acid is employed in amounts sufficient to produce a crude cyanuric acid slurry. The crude cyanuric acid slurry concentration is not critical. However, from a commercial process standpoint, slurry concentrations below about 10% or above about 45% are not desirable. Slurry concentrations below about 10% are not economical in view of the small cyanuric acid concentrations treated. Slurry concentrations above about 45% are not workable because they are difficult to handle. Accordingly, crude cyanuric acid slurry concentrations between 10 and 45% are employed, with slurry concentrations between 15 and 25% being preferred.

The aqueous phosphoric acid solution must be employed in concentrations of about 10 to about 85% by weight phosphoric acid. As the phosphoric acid concentration drops below about 10% or increases above about 85%, the rate of conversion of the cyanuric acid impurities into cyanuric acid decreases sharply, becoming negligible in pure water or in pure phosphoric acid (100%). The aqueous phosphoric acid solution is prepared from orthophosphoric acid, pyrophosphoric acid, super-phosphoric acid or combinations thereof dispersed in water to the desired phosphoric acid concentration.

Digestion of the crude cyanuric acid slurry must be carried out at a temperature of about 180° to about 220° C. At temperatures of about 180° to about 220° C, the reaction rate is very rapid and substantially all of the cyanuric acid impurities are converted to cyanuric acid. At temperatures below about 180° C, the reaction rate is slow and the amount of ammelide converted to cyanuric acid is significantly decreased. At temperatures above about 220° C, phosphoric acid catalyzes the thermal decomposition of cyanuric acid, thus substantially decreasing cyanuric acid yields. Optimum reaction rate and optimum ammelide conversion occurs at the preferred temperatures of about 195° to about 217° C.

Digestion of the crude cyanuric acid slurry must be carried out under pressure in order to prevent water vaporization losses. The pressure, however, is not critical and the autogenously developed pressure at the various reaction temperatures is normally used. Generally, the autogenously developed pressure will vary from about 130 to about 275 p.s.i.g. at reaction temperatures of about 182° to about 217° C respectively.

The time period required for the reaction to be maintained at the desired operating temperature is not critical. Once the reaction mass reaches the particular operating temperature, the crude cyanuric acid impurities immediately begin forming cyanuric acid. Maximum conversion, that is over 90%, of the cyanuric acid impurities to cyanuric acid have been obtained in the laboratory in reaction times up to about 60 seconds. Reactiom times longer than 60 seconds have not significantly increased the percentage of impurity converted. However, from a commercial standpoint, reaction times up to about 10 minutes and preferably 1 to 5 minutes are employed when conventional pressure reactors are used. Shorter reaction times, that is reaction times up to 60 seconds, may be commercially feasible with commercially available pipe reactors. A pipe reactor is an elongated tubular reaction chamber wherein the feed enters the reactor in one end and exits out the other end. The reaction takes place within the tube which is heated by external sources. Use of pipe reactors greatly increases the production of purified cyanuric acid and eliminates the need for large, expensive reactors currently used.

The use of phosphoric acid to purify crude cyanuric acid in high yields at high reaction temperatures, and in relatively short reaction periods is highly unexpected. It is unexpected because phosphoric acid is a relatively weak mineral acid as is apparent from its dissociation constants ($pK_1$ is 2.12, $pK_2$ is 7.21, and $pK_3$ is 12.32) as compared to the fully dissociable strong mineral acids conventionally employed, such as sulfuric acid ($pK_1$ is 0.40 and $pK_2$ is 1.92), hydrochloric acid and nitric acid. It is also unexpected since only one hydrogen ion is available from phosphoric acid for catalyzing the hydrolysis of ammelide whereas two hydrogen ions are available from sulfuric acid. Furthermore, it was unexpected because the ionization of $K_1$ is not appreciably increased as a function of temperature. In contrast, the ionization of the strong mineral acids is increased at increased reaction temperatures.

Mixing of the crude cyanuric acid with the aqueous phosphoric acid solution and heating mixture to the desired operating temperature are achieved by conventional means and procedures. Mixing and heating may be done separately or carried out in a single stage. For example, when mixing and heating are done separately, the crude cyanuric acid is mixed with water to form a slurry of cyanuric acid, the slurry is placed in a pressure vessel and heated to the desired temperature. The aqueous phosphoric acid solution is then passed into the pressure vessel, mixed with the crude cyanuric acid, and the reaction takes place. When mixing and heating are carried out in a single stage process, crude cyanuric acid, in either dry, moist or water slurried form is added to the aqueous phosphoric acid solution, mixed, and passed into a reactor which is previously or subsequently heated to the desired temperature. The reaction is then permitted to go to completion. Alternate procedures may likewise be employed.

When the acid digestion reaction is complete, the hot digested cyanuric acid is cooled by any conventional means to precipitate the cyanuric acid crystals. The crystals are then recovered from the acid digestion solution by any desirable means. One process that may be employed to recover the cyanuric acid crystals is disclosed in U.S. Pat. No. 3,107,244. In this process the acid digestion solution is cooled to a temperature above about 57° C to precipitate anhydrous cyanuric acid crystals. The precipitated crystals are then separated from the digestion solution by filtration at a temperature above about 57° C. The separated crystals are then washed with hot water at a temperature above about 57° C, and the washed cyanuric acid crystals are recovered. Alternative methods for precipitating and recovering cyanuric acid crystals may also be employed.

The recovered cyanuric acid crystals may then be dried and stored, or passed directly to a chlorinator and converted into chloroisocyanuric acids. The conversion of cyanuric acid into chloroisocyanuric acids, such as dichloroisocyanuric acid and/or trichloroisocyanuric acid is well known in the art and does not constitute part of this invention.

Drying may be carried out in any conventional manner in order to remove residual moisture and to produce a free-flowing crystalline product. Preferably, the crystals are heated to temperatures of at least 120° C.

Removal of the digestion solution from the cyanuric acid crystals results in crystals that can be handled easily and prevents the formation of hard cement-like masses of cyanuric acid. However, removal of all of the digestion solution from the crystals is not commercially feasible. In has been determined that removal of all but residual trace amounts of digestion solution from the crystals produces a commercially satisfactory product. These residual trace amounts of digestion solution remaining on the crystals must generally constitute less than 0.1% by weight, and preferably about 0.01 to about 0.08% by weight phosphate values (phosphoric acid and phosphate salts, such as ammonium phosphate). These minor traces of digestion solution do not adversely affect the quality or utility of the cyanuric acid crystals.

The separated digestion solution contains most of the dissolved impurities, ammonium salts, and excess phosphoric acid. The entire digestion solution or portions thereof may be sporadically or continuously recycled to the digester. The portion of the digestion solution not recycled is conveniently treated to produce phosphate containing compounds. The most economical phosphate containing compounds to produce are ammonium phosphate compounds which are readily utilized as fertilizers. Processes for producing ammonium phosphate fertilizers are well known and are described in the literature. By treating the digestion solution in this manner, pollution abatement is readily achieved and vital by-products are produced.

The process of the invention may be carried out in a batch type manner or continuously with or without recycle. A once-through acid digestion system is preferable to a recycle system since the former system improves control over the entire process by eliminating the maintenance necessary to monitor and adjust phosphoric acid concentrations during digestion of the crude cyanuric acid.

The cyanuric acid crystals produced according to the process of this invention are novel, large, well-defined, free-flowing crystals. Crystal size has been unexpectedly discovered to be a function of phosphoric acid concentration. For example, when the aqueous phosphoric acid solution contains about 10 to about 30% phosphoric acid, at least 90% of the cyanuric acid crystals recovered have particle sizes between 400 and 650 microns. When the aqueous phosphoric acid solution contains about 30 to about 85% phosphoric acid, at least 90% of the cyanuric acid crystals recovered have particle sizes between 60 and 100 microns. These crystals are 2 to 8 times larger than conventionally prepared cyanuric acid crystals. The direct formation of large crystals permits the crystals to be recovered in an easy and efficient manner without the need for careful controls to prevent cyanuric acid losses formerly attributable to conventional separating equipment. Furthermore, the crystals produced according to the present invention have frangibility values substantially equal to conventionally prepared crystals. This property permits the crystals to be handled, shipped and stored easily without the difficulties associated with dusting.

The invention will be better understood from a consideration of the following examples, and a reference to the attached illustrations. The examples are given to illustrate the invention, and are not deemed to be limiting thereof. All percentages given are based upon weight unless otherwise indicated. The illustrations are reflective photomicrographs of cyanuric acid crystals which clearly demonstrate the invention described and claimed herein, and are identified as follows.

FIG. 1 shows crystals of cyanuric acid formed by purifying crude cyanuric acid with phosphoric acid. The photomicrograph was taken at 15 X magnification.

Figure 2:
FIG. 2 is a photomicrograph of cyanuric acid crystals formed from crude cyanuric acid digested with sulfuric acid.

FIG. 2 shows crystals of cyanuric acid formed by purifying crude cyanuric acid with sulfuric acid. The photomicrograph was taken at 15 X magnification.

EXAMPLE 1

This example demonstrates the effect temperature has on the percentage of ammelide converted to cyanuric acid.

Inventive Runs 1, 2, and 3

A 25.8 gram (0.2 mole) sample of crude cyanuric acid prepared from urea assaying about 80% cyanuric acid and about 20% ammelide was mixed with 92.1 grams of water to form a 17.3% slurry. The slurry was charged into a 300 milliliter Hastelloy B autoclave. The autoclave was sealed, shaken, and heated to a temperature of approximately 6° C less than the reaction temperatures recited in Table I, Runs 1, 2, and 3. A 27.9 gram sample of 20% orthophosphoric acid was then blown into the autoclave under pressure. The phosphoric acid addition took place in less than 2 seconds. Upon acid addition, the reaction temperature immediately rose to the temperatures recited in Table I, Runs 1, 2, and 3. The reaction temperature was maintained for one minute. The autoclave was then quenched in an ice bath and rapidly cooled to 80° C within 30 seconds. The reaction mixture was removed from the autoclave at room temperature and the crystallized cyanuric acid was filtered from the slurry. The filtered cyanuric acid crystals and separated filtrate was then analyzed for cyanuric acid and ammelide content. The results are set forth in Table I.

Comparative Run A

A 25.8 gram (0.2 mole) sample of crude cyanuric acid prepared from urea assaying about 80% cyanuric acid and about 20% ammelide was mixed with 27.9 grams of 20% orthophosphoric acid. The slurry was charged into a 200 milliliter three-necked flask equipped with a magnetic stirrer, thermometer, and condenser, and refluxed at 104° C for 240 minutes. The mixture was then cooled rapidly and filtered according to Example 1, and the filtered cyanuric acid crystals and separated filtrate was then analyzed for cyanuric acid and ammelide content. The results are set forth in Table I.

TABLE I

| Run No. | Time (minutes) | Reaction Temperature ° C | Reaction Pressure p.s.i.g. | Total Analysis % Cyanuric acid | % Ammelide | % Ammelide Conversion |
|---|---|---|---|---|---|---|
| Run 1 | 1 | 182 | 130 | >99.9 | trace | 90.1 |
| Run 2 | 1 | 196 | 200 | >99.9 | trace | 96.4 |
| Run 3 | 1 | 206 | 240 | >99.9 | trace | 99.0 |
| Comparative Run A | 240 | 104° C | 0 | 92.1 | 7.9 | 46.5 |

">" means greater than

EXAMPLE 2

This example demonstrates the effect of reaction time on the percentage of ammelide converted to cyanuric acid.

Inventive Runs 4 and 5

The procedure of Example 1, Run 1 was repeated in Run 4 except that the reaction temperature was maintained at 182° C for 2 minutes. The procedure of Example 1 was repeated in Run 5 except that the sealed autoclave was heated to 198° C and the phosphoric acid addition took place in less than 6 seconds, and the reaction temperature was maintained for 5 seconds after phosphoric acid addition. At the end of 5 seconds, the autoclave was cooled and the contents removed, separated and analyzed according to Example 1. The results are set forth in Table II.

TABLE II

| Example | Run No. | Time (seconds) | Reaction Temperature °C | Total Analysis % Cyanuric Acid | % Ammelide | % Ammelide Conversion |
|---|---|---|---|---|---|---|
| 1 | 1 | 60 | 182 | >99.9 | trace | 90.1 |
| 2 | 4 | 120 | 182 | >99.9 | trace | 90.5 |
| 2 | 5 | 5 | 198 | >99.9 | trace | 91.3 |

">" means greater than

EXAMPLE 3

This example demonstrates the effect of phosphoric acid concentration and types of phosphoric acid employed on the percentage of ammelide converted to cyanuric acid. This example also demonstrates the effect of phosphoric acid concentration on cyanuric acid crystal size.

Inventive Runs 6 through 12

The procedure of Example 1 was repeated at a reaction temperature of 197° C and pressure of 180 p.s.i.g. with various concentrations of ortho and superphosphoric acid. The results are set forth in Table III.

Comparative Runs B and C

The procedure of Example 1 was repeated except in comparative Run B no phosphoric acid was added and in comparative Run C a solution of 100% phosphoric acid was added. The results are set forth in Table III.

EXAMPLE 4

This example compares cyanuric acid crystals produced according to the present invention with cyanuric acid crystals produced under identical conditions with sulfuric acid.

Inventive Run 13

A 25.8 gram (0.2 mole) sample of crude cyanuric acid prepared from urea assaying about 80% cyanuric acid and about 20% ammelide was mixed with 92.1 grams of water to form a 17.3% slurry. The slurry was charged into a 300 milliliter Hastelloy B autoclave. The autoclave was sealed, shaken, and heated to 192° C. A 27.9 gram sample of 20% phosphoric acid was then blown into the autoclave under pressure. The phosphoric acid addition took place in less than 2 seconds. Upon acid addition, the reaction temperature immediately rose to 198° C. The reaction temperature was maintained for one minute. The autoclave was then quenched in an ice bath and rapidly cooled to 80° C within 30 seconds. The reaction mixture was removed from the autoclave at room temperature and the crystallized cyanuric acid was filtered from the slurry. The recovered cyanuric acid crystals are illustrated in FIG. 1. The product had a bulk density of 32 lb/ft³ and had at least 90% cyanuric acid crystals with particle sizes between 400 and 650 microns.

Comparative Run D

The procedure of Inventive Run 13 was repeated except that 20% sulfuric acid was used instead of 20% phosphoric acid. The cyanuric acid cyrstals are illustrated in FIG. 2. The product had a bulk density of 37 lb/ft³ and had at least 90% cyanuric acid crystals with particle sizes between 100 and 200 microns. The cyanuric acid crystals produced from Inventive Run 13 and Comparative Run D both had substantially identical frangibilities.

TABLE III

| Run No. | Time (min.) | % H₃PO₄ Concentration | Form of Phosphoric Acid | % Ammelide Conversion | Cyanuric Acid Crystal Size |
|---|---|---|---|---|---|
| 6 | 1 | 11 | ortho | 96.7 | > 90% of crystals recovered had particle sizes between 400 and 650 microns |
| 7 | 1 | 20 | ortho | 96.4 | same as Run 6 |
| 8 | 1 | 50 | ortho | 95.5 | > 90% of crystals recovered had particle sizes between 60 and 100 microns |
| 9 | 1 | 65 | ortho | 98.2 | same as Run 8 |
| 10 | 1 | 65 | super* | 98.0 | same as Run 8 |
| 11 | 1 | 75 | ortho | 95.5 | same as Run 8 |
| 12 | 1 | 75 | super* | 95.6 | same as Run 8 |
| Comparative B | 1 | 0 | none | 0.0 | 30 to 50 microns |
| C | 1 | 100 | super* | 0.0 | 30 to 50 microns |

">" means greater than
*mixture of pyro and ortho

The invention being thus described, it will be obvious that the same may be varied in many ways. Such variations are not to be regarded as a departure from the spirit and scope of the invention, and all such modifications are intended to be included within the scope of the following claims.

What is claimed is:

1. A novel free-flowing cyanuric acid composition having at least 90% cyanuric acid crystals with particle sizes between 400 and 650 microns and containing about 0.01 to about 0.08% phosphate values produced by mixing sufficient amounts of crude cyanuric acid with an aqueous phosphoric acid solution containing about 10 to about 30% phosphoric acid to form a 10 to 45% crude cyanuric acid slurry;

heating the slurry to a temperature of about 180° to about 220° C under at least the autogenously developed pressure to digest the crude cyanuric acid;

cooling the digested cyanuric acid to precipitate the cyanuric acid crystals; and recovering the novel cyanuric acid composition.

* * * * *